United States Patent [19]

Levy et al.

[11] 4,360,007

[45] Nov. 23, 1982

[54] REMOTE CONTROLLED MAGNETIC ACTUATOR PARTICULARLY FOR AN IMPLANTABLE DEVICE LIKE A VALVE

[75] Inventors: Itshak Levy, Ramat Gan; Samuel Ron, Ramat Hasharon; Abraham Sahar, Jerusalem; Jehoshua Wolowelsky, Ramat Gan, all of Israel

[73] Assignee: Yeda Research and Development Co., Ltd., Rehovot, Israel

[21] Appl. No.: 175,499

[22] Filed: Aug. 5, 1980

[51] Int. Cl.³ ............................................. A61B 19/00
[52] U.S. Cl. ...................................... 128/1 R; 251/7; 251/230; 251/205; 74/142; 128/274; 128/DIG. 25
[58] Field of Search ..................... 74/50, 142; 251/230, 251/7, 205; 128/1 R, 346, 274, DIG. 25

[56] References Cited

U.S. PATENT DOCUMENTS

| | | | |
|---|---|---|---|
| 802,959 | 10/1905 | Waterman | 251/230 |
| 2,431,836 | 12/1947 | Snyder et al. | 251/230 |
| 3,419,008 | 12/1968 | Plishner | 128/DIG. 25 |
| 3,817,237 | 6/1974 | Bolduc | 128/DIG. 25 |
| 4,014,318 | 5/1977 | Dockum et al. | 128/1 D |
| 4,024,855 | 5/1977 | Bucalo | 128/1 R |
| 4,266,697 | 5/1981 | Zissimopoulos | 222/450 |

FOREIGN PATENT DOCUMENTS 2806405  8/1978  Fed. Rep. of Germany ... 128/DIG. 25

Primary Examiner—A. Michael Chambers
Attorney, Agent, or Firm—Browdy and Neimark

[57] ABSTRACT

An actuator device comprising a housing in which there is arranged a permanent magnet extending at 90° from an axially supported member, said member being attached to a driving pawl via a springy leaf, the movement of said magnet being limited by two stop members attached to the bottom plate of the housing, a ratchet wheel with a plurality of teeth pointing downwards and adapted to be engaged by said pawl, another pawl attached to a springy member rigidly attached to said housing, the pawl being adapted to stop a reverse movement of the ratchet wheel, the arrangement being such that application of a magnetic field of adequate strength from a certain distance results in the movement of the magnet and the pawl attached thereto within the range defined by the stop members, each such movement resulting in the stepwise advance of the ratchet wheel by one tooth.

7 Claims, 5 Drawing Figures

REMOTE CONTROLLED MAGNETIC ACTUATOR PARTICULARLY FOR AN IMPLANTABLE DEVICE LIKE A VALVE

FIELD OF THE INVENTION

The invention relates to actuator means actuated from a distance by means of a magnetic field, resulting in a rotational or in any other desired motion resulting from such rotational movement of part of the actuator.

The novel actuator is especially suitable for implantation in the human body and for actuation from the outside by a magnetic field. Such actuator can be used for controlling various devices and appliances.

BACKGROUND OF THE INVENTION

Various devices are implanted into the human body. Sometimes it is required to transmit motion into these devices for purposes of regulation or other reasons. One of the possible ways of accomplishing this requirement is by means of two magnets, one implanted, and a strong external one used for actuating the implanted one. The outside magnet, also termed a "driver" is generally a powerful electromagnet, while the implanted, driven one, is a small permanent magnet which follows the movement of the driver and thus performs the various tasks.

It is generally required that the movement of the implanted member be controlled in an accurate manner. This requires speed reduction means and locking means so as to maintain the driven member is a certain position after the driver has been removed and shut off. It is also required that a predetermined position of the driven member can be easily reached in an accurate manner.

SUMMARY OF THE INVENTION

The invention relates to an implantable actuator, driven from a distance by application of a suitable magnetic field. Means are provided for moving a ratchet wheel which forms part of the actuator in a controlled stepwise manner, the movement per step being determined by the subdivision of the ratchet, which is generaly in such manner that after a number of steps the starting position is reached again. The actuator comprises a permanent magnet connected to a driving pawl by an elastic leaf, a ratchet wheel and a locking pawl, the arrangement being such that each movement of the permanent magnet upon application of an external magnetic field of adequate strength results in the rotation of the ratchet wheel by the angle of one of its teeth, repeated applications of the magnetic field resulting in a stepwise rotation of said ratchet wheel.

When the magnet of the actuator is subjected to the influence of the external magnetic field, it tends to align itself in the direction of said field. The extent of this movement is limited by stop members to a rotation which corresponds to the angle of one tooth of the ratchet wheel. At this stage the magnetic field can be removed and the ratchet will remain in the given position. If it is intended to continue with the rotational movement of the ratchet wheel, the polarity of the magnetic field is reversed, the magnet of the actuator rotates back to its starting position, but a pawl prevents any backward movement of the ratchet wheel. The rotational movement of the ratchet wheel upon repeated application of the external magnetic field can be easily be translated by mechanical means to a lateral movement.

When the ratchet is divided into "n" teeth, each defining 360°:n degrees, after "n" cycles, i.e. reversals of the magnetic field, the ratchet wheel will return to its initial position, the movement per step being 360°:n degrees.

Amongst the advantages of the novel actuator there may be mentioned the simplicity of construction and its reliability. It is of small size, and can easily be implanted. The ratchet wheel remains in a given position unless a predetermined strong external magnetic field is applied. The exact position of the wheel is known according to the number of magnetic pulses applied, and it is also possible to provide means for inspection by X-rays. Backward movement is prevented, but it is possible to revert to any given position by application of a predetermined number of steps (pulses).

DESCRIPTION OF A PREFERRED EMBODIMENT

The invention is illustrated by way of example only with reference to the enclosed schematical drawings, which are not according to scale and in which.

Figure 1:
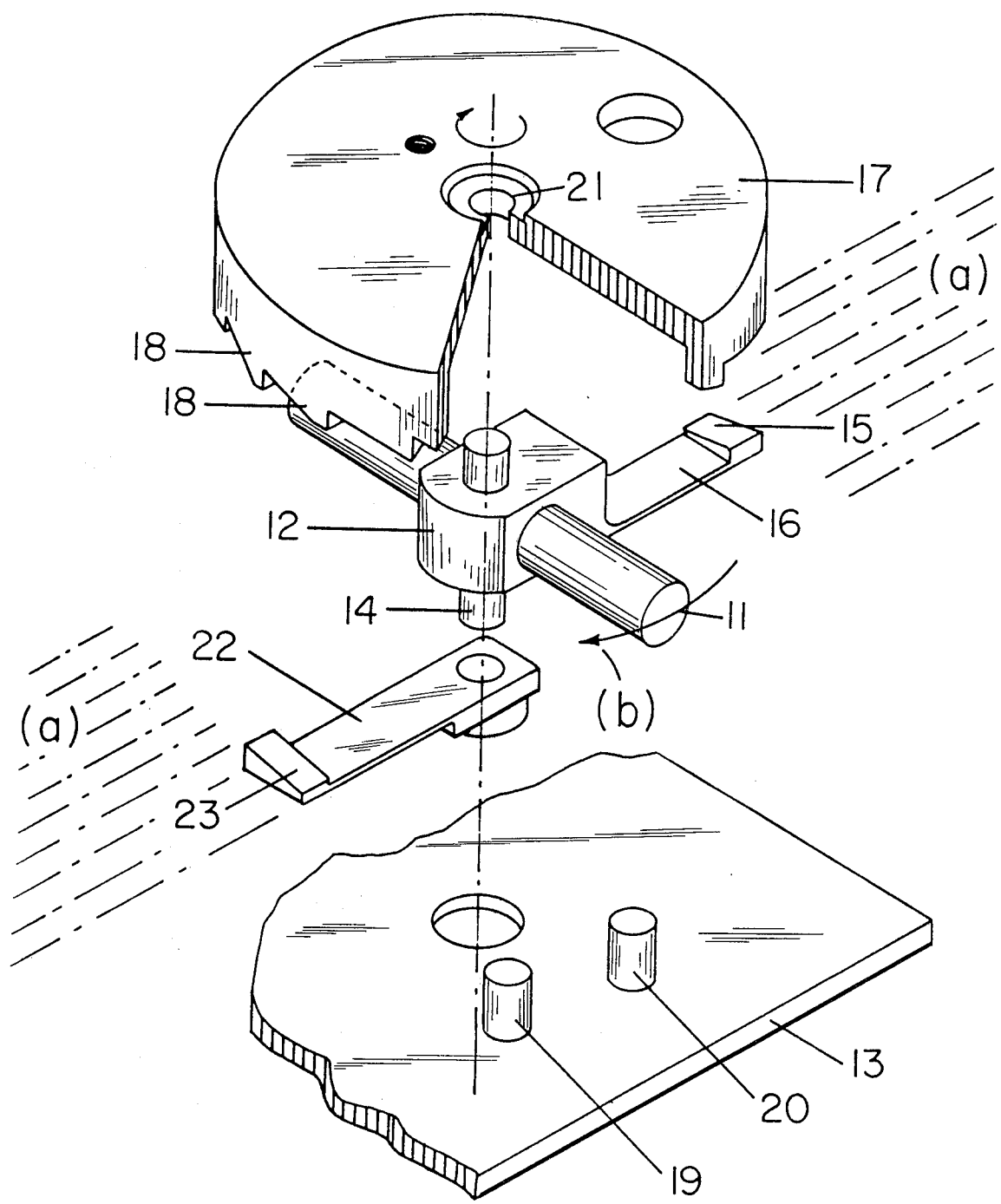
FIG. 1 is an exploded perspective view of an actuator according to the invention.
Figure 2:
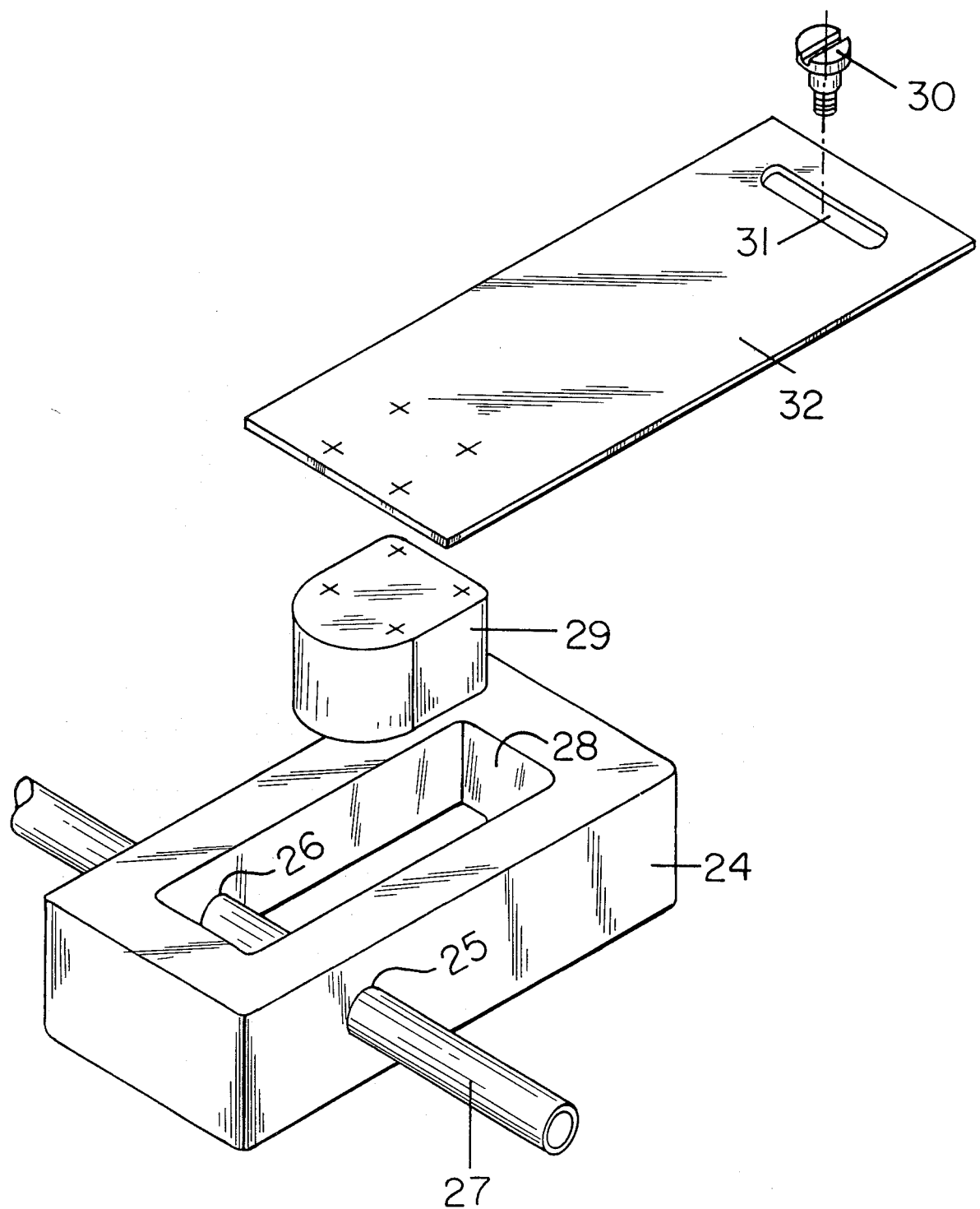
FIG. 2 illustrates a pinch valve actuated by an actuator according to the invention.
Figure 3:
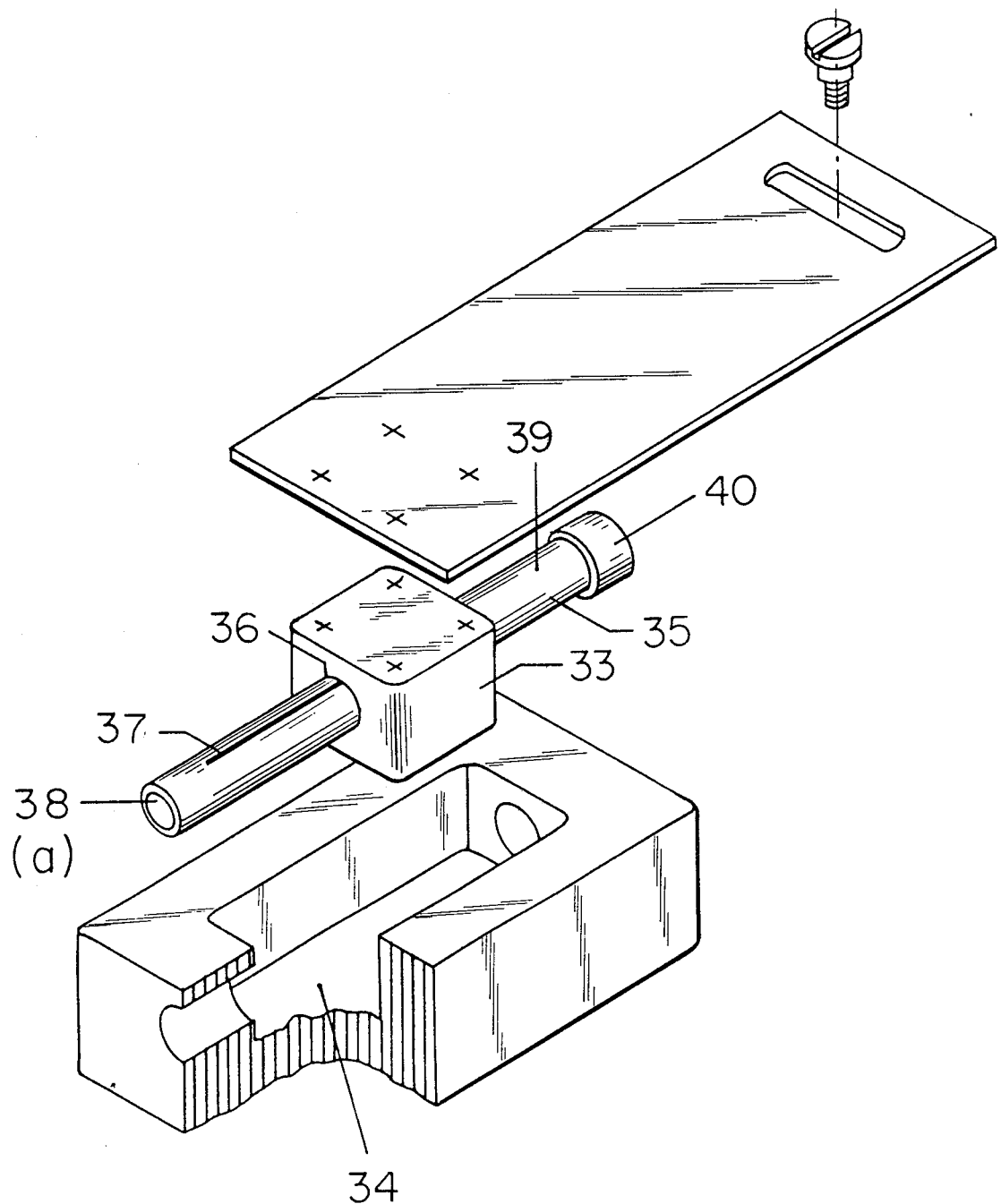
Figure 4:
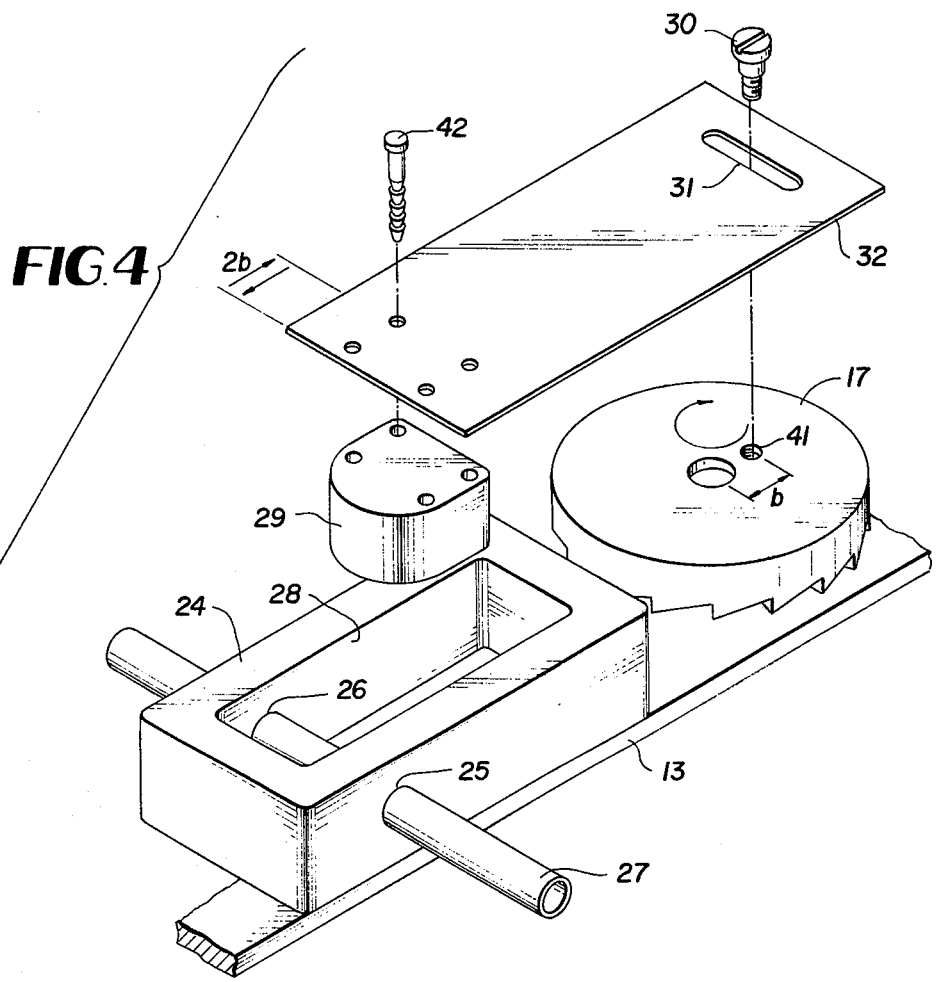
Figure 5:
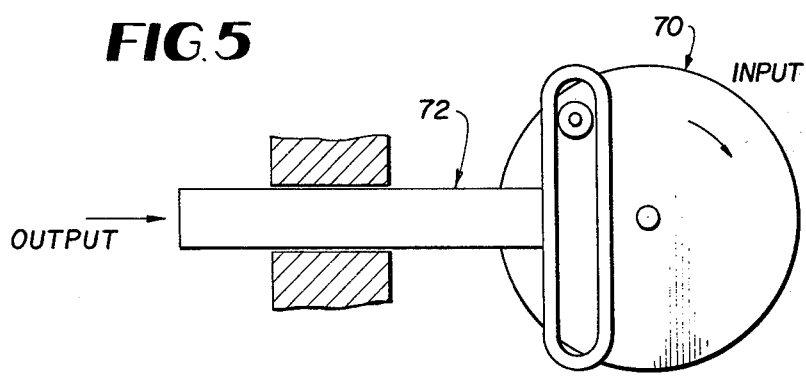

FIG. 3 illustrates a slit valve controlled by an actuator according to the invention; and FIG. 4 illustrates the cooperative relationship between the actuator of FIG. 1 and the pinch valve of FIG. 2; and FIG. 5 illustrates the operating principle of the mechanism use in FIGS. 2 and 4. As shown in FIG. 1, an actuator according to the present invention comprises in combination a permanent magnet 11 attached to a member 12 which is mounted in a housing 13 by an axis 14, a driving pawl 15 being attached to said member 12 by an elastic leaf member 16; a ratchet wheel 17 provided with "n" teeth 18, each of a predetermined number of degrees, said teeth 18 being adapted to be engaged by said pawl 15, two stop members 19 and 20 attached to the bottom member of the housing 13, the axis 14 being rotatably mounted in a hole 21 in the ratchet wheel 17, there being provided beneath said member 12 a leaf spring 22 with pawl 23 at its outer part, said leaf spring and pawl being rigidly attached to the housing 13.

When the ratchet wheel is to be moved, an external magnetic field is applied, the field lines of which are shown as (a), and this tends to move the permanent magnet 11 (which is a strong magnet, such as a cobalt-rare-earth type magnet), in the direction of the arrow (b), until its axis will be aligned with this external field. The stops 19 and 20 limit this movement per step to the angle of one tooth 18 only. When the polarity of the external magnetic field is reversed, the magnet 11 rotates back to the starting position, while pawl 23 prevents the backward movement of the ratchet wheel 17. Each subsequent application of the external magnetic field and its reversal will result in a further step of the stepwise rotational movement of the ratchet wheel 17.

It is clear that the application of an external magnetic field of adequate strength results in a positive movement advancing the ratchet wheel by a given angle. If the wheel is subdivided into 20 steps, each movement will be by 18 degrees. If the division is into 36 teeth, each will be a movement by 10 degrees, etc. The wheel remains locked in a given position and will move neither forwards nor backwards unless such external field is applied. It has been found that with a strong permanent magnet 11, an external field of about 750 gauss is required and adequate for the intended movement. A high-frequency oscillating magnetic field caused by transformers, motors or the like will not affect the actuator. Each position is definite due to the step-wise motion, each of the steps defining a certain angular motion.

The actuator can be used for actuating any desired switching or other device which can be controlled by a certain angular position with suitable contact means being attached to the ratchet wheel. The rotary motion can be used to open or close valve means and the like.

The actuator was built of inert materials (stainless steel 316L, Teflon (T.M.) and silicon-rubber) and this can be implanted in the human body and will not cause adverse reactions. A device of 28 mm diameter and of 12 mm height gave satisfactory results. The permanent magnet was ensheathed in a sheath of stainless steel.

The following illustrates a number of devices which can be actuated by the novel device:

a. A small peristaltic pump can be driven so as to transfer small quantities of fluids. The rate of flow can be controlled by the number of steps of the ratchet wheel per unit time. This can be used for the controlled administration of any liquid medium.

b. The rotary movement can be used for controlling the position of a multi-way rotary valve.

c. The rotary movement of the ratchet can be translated by conventional mechanical means into a reciprocating linear motion. Amongst mechanical means useful for such transformation there may be mentioned "scotch-yoke" type mechanisms. Possible applications of such linear motion are illustrated with reference to FIGS. 2 and 3. FIG. 2 illustrates a pinch valve actuated by means of a "scotch yoke mechanism" (the principle of operation which is shown in FIG. 5, this being a common mechanism illustrated in many technical handbooks). The pinch valve consists of a member 24, provided with through holes 25 and 26, through which passes tubing 27, and a member 29 which at a certain position of the mechanism presses against this tubing, closing it. The actuator and the pinch valve are attached to the base plate of housing 13. Screw 30 is secured eccentrically to the ratchet wheel 17 at hole 41 shown in FIG. 4. As the ratchet wheel 17 rotates, screw 30 serves as an input crank of the mechanism, indicated at 70 in FIG. 5, while groove 31 in member 32 serves as reciprocating output yoke, indicated by output member 72 in FIG. 5. Member 32 is rigidly attached to member 29 by pins 42.

In member 24 there is provided a rectangular opening 28 into which member 29 fits slidingly. During each full rotation of the ratchet wheel 17 member 29 travels back and forth, the movement in each direction being a distance 2b, which is twice the eccentricity b of screw 30. Thus, the off-center dimension b, i.e. the eccentricity of the screw 30, is half the distance of the required linear movement of 29.

When the member 29 completes its movement towards tubing 27, it presses against this resilient tubing and closes it. Thus, during each full rotation of the ratchet wheel the valve moves from fully open to fully closed and again to the fully open position. In FIG. 2 the fully open position is illustrated.

As shown if FIG. 3, a cubical member 33 is slidingly arranged in the rectangular space 34, and on rubber tubing 35, which passes through a cylindrical hole 36 of member 33, a slot 37 being provided in tubing 35. The reciprocating movement of member 33 on the tubing results in a gradual opening up of the slot 37 and in its closure as the direction of movement of member 33 is reversed. The fluid enters tubing 35 at its open end 38, while end 39 is closed by closure 40. The change of position of member 33 results in a change of exposed length of slot 37 thus changing the rate of discharge of the fluid through said slot from zero up to a predetermined value.

While the invention has been described in detail above, it is to be understood that this detailed description is by way of example only, and the protection granted is to be limited only within the spirit of the invention and the scope of the following claims.

We claim:

1. An actuator device comprising a housing in which there is arranged a permanent magnet extending at 90° from an axially supported member, said member being attached to a driving pawl via a springy leaf, the movement of said magnet being limited by two stop members attached to the bottom plate of the housing, a ratchet wheel with a plurality of teeth pointing downwards and adapted to be engaged by said pawl, another pawl attached to a springy member rigidly attached to said housing, the pawl being adapted to stop a reverse movement of the ratchet wheel, the arrangement being such that application of a magnetic field of adequate strength from a certain distance results in the movement of the magnet and the pawl attached thereto to or fro within the range defined by the stop members, each such movement resulting in the stepwise advance of the ratchet wheel by one tooth.

2. A device according to claim 1, wherein the ratchet wheel is divided into a number of teeth each being an equal subdivision of 360°.

3. An actuator according to claim 1, provided with an eccentric screw on the upper surface of the ratchet wheel adapted to convert the rotary movement of said rachet wheel to a reciprocating movement.

4. An actuator according to claim 1, for implantation into the human body, made of biologically inert materials or covered with such materials.

5. A device according to claim 1, wherein the magnet is a cobalt-rare-earth magnet.

6. An actuator device according to claim 1, in combination with a pinch valve including means converting the rotary movement of the actuator into a reciprocating movement, resulting in a change from fully open to totally closed position of a resilient tubing which controls the flow of a liquid valved by said pinch valve.

7. An actuator device according to claim 1, in combination with a slit valve, wherein the reciprocating movement of a member is obtained by the rotation of the actuator, said reciprocating movement resulting in the opening up and closing of a slit in a rubber tubing, controlling the flow of a liquid through said slit.

* * * * *